(12) United States Patent
Hitchems et al.

(10) Patent No.: US 6,468,953 B1
(45) Date of Patent: Oct. 22, 2002

(54) METHODS OF PREPARING ANTIMICROBIAL COMPOSITIONS COMPRISING OZONE

(75) Inventors: G. Duncan Hitchems, Bryan; Steven Drabek; Anthony Giletto, both of College Station; Charles Blankenburg, Bryan; Kyle B. Uselton; Jennifer Schultz-Bathurst, both of College Station, all of TX (US); Shivaun Archer, Ithaca, NY (US)

(73) Assignee: Lynntech, Inc., College Station, TX (US)

( * ) Notice: Subject to any disclaimer, the term of this patent is extended or adjusted under 35 U.S.C. 154(b) by 0 days.

(21) Appl. No.: 09/631,867

(22) Filed: Aug. 3, 2000

(51) Int. Cl.$^7$ ................................. C11D 17/00
(52) U.S. Cl. ................... 510/218; 510/477; 510/488; 510/505
(58) Field of Search ................. 510/161, 218, 510/477, 488, 505

(56) References Cited

U.S. PATENT DOCUMENTS

| | | |
|---|---|---|
| 4,129,517 A | 12/1978 | Eggensperger et al. |
| 4,287,130 A | 9/1981 | Dohm et al. |
| 4,404,040 A | 9/1983 | Wang |
| 4,865,759 A | 9/1989 | Coyne et al. |
| 5,074,960 A | 12/1991 | Nimz et al. |
| 5,089,167 A | 2/1992 | Coyne et al. |
| 5,292,941 A | 3/1994 | Kigawa et al. |
| 5,567,444 A | 10/1996 | Hei et al. |
| 5,575,947 A | 11/1996 | Venturello et al. |
| 5,674,538 A | 10/1997 | Lokkesmoe et al. |
| 5,900,256 A | 5/1999 | Scoville, Jr. et al. |
| 5,945,391 A | 8/1999 | Yant et al. |
| 6,008,405 A | 12/1999 | Gray et al. |
| 6,010,729 A | 1/2000 | Gutzmann et al. |
| 6,200,618 B1 | 3/2001 | Smith et al. |

FOREIGN PATENT DOCUMENTS

| | | |
|---|---|---|
| EP | 0 233 731 A2 | 8/1997 |
| WO | WO 01/05702 A1 | 1/2001 |

*Primary Examiner*—Necholus Ogden
(74) *Attorney, Agent, or Firm*—Street & Steele; Jeffrey L. Streets

(57) ABSTRACT

The invention relates to the formation of antimicrobial solutions formed by ozonating a liquid containing organic precursor molecules. The preferred organic precursor molecules include carboxylic acids, most particularly octanoic acid with or without acetic acid, and alcohols, most particularly greater than 80 weight percent ethanol. The ozonating step is preferably performed with minimal or no water present in the liquid containing the organic precursors. After ozonation is complete, the ozonated liquid may be diluted with water or other solvent to form a use solution for contacting and cleaning a microbially contaminated surface or other medium.

45 Claims, 14 Drawing Sheets

Effect of ozonated octanoic acid in acetic acid: effect on *Bacillus subtilis* spores

| | ozone treatment time (min) | dilution factor | log$_{10}$ pre-disinfec | log$_{10}$ reduction | fraction of carriers with positive growth |
|---|---|---|---|---|---|
| control treatments (no ozone) | | | | | |
| AAc 81% | 0 | undiluted | 7.41 | 3.37 | 3/3 |
| AAc 81% | 0 | undiluted | 7.60 | 2.87 | 3/3 |
| OAc 15% in AAc | 0 | 1:3 | 7.21 | 0.39 | 3/3 |
| OAc 15% in AAc | 0 | 1:9 | 7.21 | 0.73 | 3/3 |
| glutaraldehyde 2% | 0 | undiluted | 7.28 | 4.12 | 3/3 |
| " | 0 | undiluted | 7.04 | 3.29 | 3/3 |
| " | 0 | undiluted | 7.56 | 3.15 | 3/3 |
| ozone treated solutions | | | | | |
| AAc 100% | 90 | 1:3 | 7.62 | 2.60 | 3/3 |
| AAc 100% | 90 | 1:9 | 7.62 | 2.03 | 3/3 |
| OAc 15% in AAc | 10 | 1:3 | 7.21 | >6.21 | 0/3 |
| OAc 15% in AAc | 10 | 1:9 | 7.21 | 4.08 | 3/3 |
| OAc 15% in AAc | 10 | 1:27 | 7.60 | 5.59 | 1/3 |
| OAc 15% in AAc | 10 | 1:81 | 7.60 | 2.99 | 3/3 |
| OAc 15% in AAc | 30 | 1:3 | 7.21 | >6.21 | 0/3 |
| OAc 15% in AAc | 30 | 1:9 | 7.21 | >6.21 | 0/3 |
| OAc 15% in AAc | 30 | 1:27 | 7.60 | 3.94 | 2/3 |
| OAc 15% in AAc | 30 | 1:81 | 7.60 | 3.34 | 3/3 |
| OAc 15% in AAc | 90 | 1:3 | 7.21 | >6.21 | 0/3 |
| OAc 15% in AAc | 90 | 1:9 | 7.21 | >6.21 | 0/3 |
| OAc 15% in AAc | 90 | 1:27 | 7.60 | >6.60 | 0/3 |
| OAc 15% in AAc | 90 | 1:81 | 7.60 | >5.05 | 1/3 |

OAc = octanoic acid; AAc = acetic acid

Fig. 1  Effect of ozonated octanoic acid in acetic acid: effect on Bacillus subtilis spores

| | ozone treatment time (min) | dilution factor | log10 pre-disinfec | log10 reduction | fraction of carriers with positive growth |
|---|---|---|---|---|---|
| control treatments (no ozone) | | | | | |
| AAc 81% | 0 | undiluted | 7.41 | 3.37 | 3/3 |
| AAc 81% | 0 | undiluted | 7.60 | 2.87 | 3/3 |
| OAc 15% in AAc | 0 | 1:3 | 7.21 | 0.39 | 3/3 |
| OAc 15% in AAc | 0 | 1:9 | 7.21 | 0.73 | 3/3 |
| glutaraldehyde 2% | 0 | undiluted | 7.28 | 4.12 | 3/3 |
| " | 0 | undiluted | 7.04 | 3.29 | 3/3 |
| " | 0 | undiluted | 7.56 | 3.15 | 3/3 |
| ozone treated solutions | | | | | |
| AAc 100% | 90 | 1:3 | 7.62 | 2.60 | 3/3 |
| AAc 100% | 90 | 1:9 | 7.62 | 2.03 | 3/3 |
| OAc 15% in AAc | 10 | 1:3 | 7.21 | >6.21 | 0/3 |
| OAc 15% in AAc | 10 | 1:9 | 7.21 | 4.08 | 3/3 |
| OAc 15% in AAc | 10 | 1:27 | 7.60 | 5.59 | 1/3 |
| OAc 15% in AAc | 10 | 1:81 | 7.60 | 2.99 | 3/3 |
| OAc 15% in AAc | 30 | 1:3 | 7.21 | >6.21 | 0/3 |
| OAc 15% in AAc | 30 | 1:9 | 7.21 | >6.21 | 0/3 |
| OAc 15% in AAc | 30 | 1:27 | 7.60 | 3.94 | 2/3 |
| OAc 15% in AAc | 30 | 1:81 | 7.60 | 3.34 | 3/3 |
| OAc 15% in AAc | 90 | 1:3 | 7.21 | >6.21 | 0/3 |
| OAc 15% in AAc | 90 | 1:9 | 7.21 | >6.21 | 0/3 |
| OAc 15% in AAc | 90 | 1:27 | 7.60 | >6.60 | 0/3 |
| OAc 15% in AAc | 90 | 1:81 | 7.60 | >5.05 | 1/3 |

OAc = octanoic acid; AAc = acetic acid

Fig. 2    Effect of ozonated octanoic acid on Bacillus subtilis spores

| Treatment solution | ozone treatment time (min) | dilution factor | $\log_{10}$ pre-disinfec | $\log_{10}$ reduction | fraction of carriers with positive growth |
|---|---|---|---|---|---|
| control treatments (no ozone) | | | | | |
| OAc 100% | 0 | 1/9 | 7.56 | 1.87 | 3/3 |
| " | 0 | 1/81 | 7.56 | 2.20 | 3/3 |
| ozone treated solutions | | | | | |
| OAc 100% | 10 | 1/9 | 7.56 | 2.73 | 3/3 |
| " | 10 | 1/81 | 7.56 | 2.30 | 3/3 |
| OAc 100% | 30 | 1/9 | 7.56 | 6.56 | 0/3 |
| " | 30 | 1/81 | 7.56 | 3.12 | 3/3 |
| OAc 100% | 90 | 1/9 | 7.56 | 6.56 | 0/3 |
| " | 90 | 1/81 | 7.56 | 6.56 | 0/3 |

OAc = octanoic acid

Fig. 3    Ozonated valeric acid: effect on B. subtillis spores

| Treatment solution | ozone contact time (min) | dilution factor | log10 pre-disinfec | log10 reduction | Fraction of carriers with positive growth |
|---|---|---|---|---|---|
| control treatments (no ozone) | | | | | |
| VAc (15%) in AAc | 0 | 1:9 | 7.62 | 1.77 | 3/3 |
| " | 0 | 1:81 | 7.62 | 1.04 | 3/3 |
| ozone treated solutions | | | | | |
| VAc (15%) in AAc | 10 | 1:9 | 7.62 | 3.34 | 3/3 |
| " | 10 | 1:81 | 7.62 | 1.58 | 3/3 |
| VAc (15%) in AAc | 30 | 1:9 | 7.62 | 3.98 | 3/3 |
| " | 30 | 1:81 | 7.62 | 1.43 | 3/3 |
| VAc (15%) in AAc | 90 | 1:9 | 7.62 | 4.36 | 3/3 |
| " | 90 | 1:81 | 7.62 | 3.01 | 3/3 |

VAc = valeric acid

Fig. 4  Inactivation of Bacillus subtilis spores: ozonated 95% ethanol solutions

| Treatment solution | ozone contact time (min) | dilution factor | $\log_{10}$ pre-disinfec | $\log_{10}$ reduction | fraction of carriers with positive growth |
| --- | --- | --- | --- | --- | --- |
| *control treatments (no ozone)* | | | | | |
| ethanol 95% | 0 | 1/3 | 7.23 | 0.70 | 3/3 |
| " | 0 | 1/9 | 7.23 | 0.77 | 3/3 |
| ethanol 18% | 0 | undiluted | 7.56 | 1.47 | 3/3 |
| ethanol 6% | 0 | undiluted | 7.56 | 0.83 | 3/3 |
| " | 0 | undiluted | 7.44 | 1.23 | 3/3 |
| glutaraldehyde (2%) | 0 | undiluted | 7.56 | 3.15 | 3/3 |
| *ozone treated solutions* | | | | | |
| ethanol 95% | 10 | 1/3 | 7.23 | 2.07 | 3/3 |
| " | 10 | 1/9 | 7.23 | 1.12 | 3/3 |
| ethanol 95% | 30 | 1/3 | 7.23 | 2.53 | 3/3 |
| " | 30 | 1/9 | 7.23 | 1.38 | 3/3 |
| ethanol 95% | 90 | 1/3 | 7.23 | 5.80 | 1/3 |
| " | 90 | 1/9 | 7.23 | 3.54 | 3/3 |
| ethanol 18% | 10 | undiluted | 7.56 | 3.52 | 3/3 |
| ethanol 6% | 10 | undiluted | 7.44 | 3.81 | 3/3 |
| ethanol 6% | 10 | undiluted | 7.56 | 2.98 | 3/3 |
| water (12 ppm O3) | 10 | undiluted | 7.21 | 1.32 | 3/3 |
| water (15 ppm O3) | 10 | undiluted | 7.04 | 1.07 | 3/3 |

Fig. 5  Inactivation of Bacillus subtilis spores: ozonated 100% ethanol

| Treatment solution | ozone contact time (min) | dilution factor | $\log_{10}$ pre-disinfec | $\log_{10}$ reduction | fraction of carriers with positive growth |
|---|---|---|---|---|---|
| *control treatments (no ozone)* | | | | | |
| ethanol 100% | 0 | 1/3 | 7.66 | 1.28 | 3/3 |
| " | 0 | 1/9 | 7.45 | 1.73 | 3/3 |
| glutaraldehyde (2%) | 0 | undiluted | 7.56 | 3.15 | 3/3 |
| *ozone treated solutions* | | | | | |
| ethanol 100% | 10 | 1/3 | 7.66 | 3.58 | 3/3 |
| " | 10 | 1/9 | 7.45 | 1.86 | 3/3 |
| ethanol 100% | 30 | 1/3 | 7.66 | 4.44 | 1/3 |
| " | 30 | 1/9 | 7.45 | 2.27 | 3/3 |
| ethanol 100% | 90 | 1/3 | 7.66 | >6.66 | 0/3 |
| " | 90 | 1/9 | 7.45 | 4.11 | 2/3 |
| ethanol 100% | 270 | 1/3 | 7.66 | >6.66 | 0/3 |
| " | 270 | 1/9 | 7.66 | >6.66 | 0/3 |
| " | 270 | 1/27 | 7.66 | >6.66 | 0/3 |
| " | 270 | 1/81 | 7.66 | 4.46 | 3/3 |

Fig. 6  Inactivation of Bacillus subtilis spores using ozonated liquids after 48 hours

| Treatment solution | ozone contact time (min) | dilution factor | log₁₀ pre-disinfec | log₁₀ reduction | Fraction of carriers with positive growth |
|---|---|---|---|---|---|
| ozone treated solutions | | | | | |
| OAc (15%) in AAc | 90 | 1:3 | 6.73 | >5.73 | 0/3 |
| " | 90 | 1:9 | 6.73 | >5.73 | 0/3 |
| " | 90 | 1:27 | 6.73 | 3.35 | 1/3 |
| " | 90 | 1:81 | 6.73 | >5.73 | 0/3 |
| OAc | 90 | 1:3 | 6.73 | 4.36 | 1/3 |
| " | 90 | 1:9 | 6.73 | 2.95 | 2/3 |
| " | 90 | 1:27 | 6.73 | 3.22 | 2/3 |
| " | 90 | 1:81 | 6.73 | 2.28 | 3/3 |

OAc = octanoic acid
AAc = acetic acid

Fig. 7  Inactivation of Bacillus subtilis spores: ozonated octanoic acid in ethanol

| Treatment solution | ozone treatment time (min) | dilution factor | $\log_{10}$ pre-disinfec | $\log_{10}$ reduction | Fraction of carriers with positive growth |
|---|---|---|---|---|---|
| *control treatments (no ozone)* | | | | | |
| OAc (15%) in ethanol | 90 | 1:3 | 7.84 | 2.20 | 3/3 |
| " | 90 | 1:9 | 7.84 | 2.00 | 3/3 |
| " | 90 | 1:27 | 7.84 | 1.79 | 3/3 |
| " | 90 | 1:81 | 7.84 | 1.96 | 3/3 |
| *ozone treated solutions* | | | | | |
| OAc (15%) in ethanol | 90 | 1:3 | 7.84 | >6.84 | 0/3 |
| " | 90 | 1:9 | 7.84 | >6.84 | 0/3 |
| " | 90 | 1:27 | 7.84 | 2.68 | 2/3 |
| " | 90 | 1:81 | 7.84 | 4.10 | 2/3 |

OAc = octanoic acid

Fig. 8  Inactivation of *Bacillus subtilis* spores: ozonated steric acid in acetic acid

| Treatment solution | ozone treatment time (min) | dilution factor | log10 pre-disinfec | log10 reduction | Fraction of carriers with positive growth |
|---|---|---|---|---|---|
| *control treatments (no ozone)* | | | | | |
| SAc (15%) in AAc | 0 | 1:9 | 7.43 | 1.47 | 3/3 |
| " | 0 | 1:81 | 7.43 | 0.88 | 3/3 |
| *ozone treated solutions* | | | | | |
| SAc (15%) in AAc | 10 | 1:9 | 7.43 | 1.19 | 3/3 |
| " | 10 | 1:81 | 7.43 | 0.95 | 3/3 |
| SAc (15%) in AAc | 30 | 1:9 | 7.43 | 5.18 | 1/3 |
| " | 30 | 1:81 | 7.43 | 0.52 | 3/3 |
| SAc (15%) in AAc | 90 | 1:9 | 7.43 | >6.43 | 0/3 |
| " | 90 | 1:81 | 7.43 | 1.36 | 2/3 |

SAc = steric acid
AAc = acetic acid

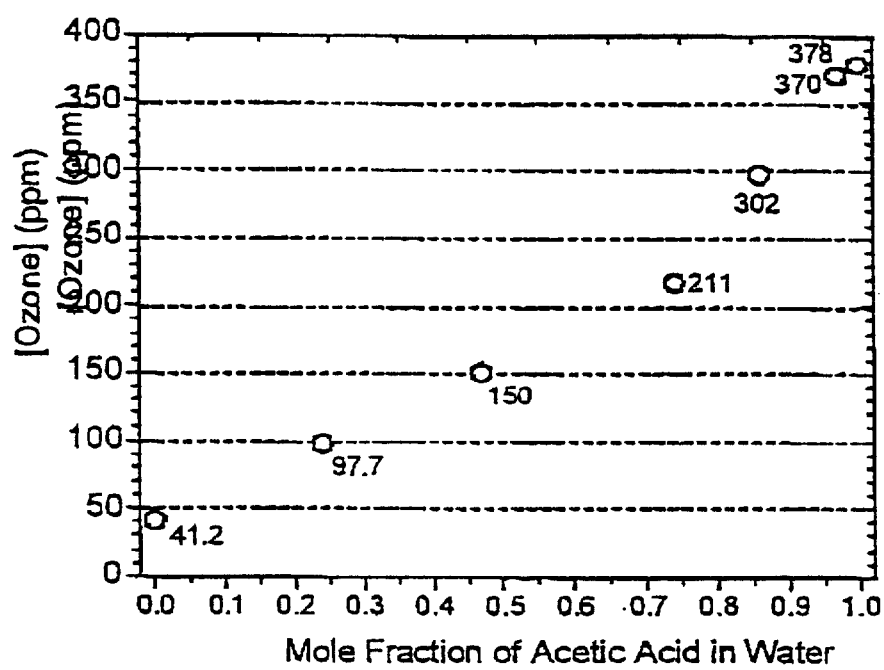
Fig. 9  High concentrations of dissolved ozone can be stored in concentrated acetic acid.

| Acid Diluted | Ozonated glacial acetic acid (0 hours). Zone size (mm) | Ozonated glacial acetic acid (16 hours). Zone size (mm) | Glacial acetic acid Zone size (mm) |
|---|---|---|---|
| 50 % | 32 | 28 | 28.5 |
| 25 % | 23.5 | 22.5 | 22 |
| 12.5 % | 20 | 17.5 | 17 |
| 6.2 % | 16 | 16 | No zone |
| 3.1 % | 16.5 | 15 | No zone |
| 1.6 % | 15 | No zone | No zone |

Fig. 10   Zone of inhibition test for ozonated and unozonated glacial acetic acid Fig. 11  Deactivation of *Bacillus subtillis* spores using ozonated acetic acid

|  | Initial ozone concentration (ppm) | log10 pre-disinfec | log10 reduction | Fraction of carriers with positive growth |
|---|---|---|---|---|
| *control treatments (no ozone)* | | | | |
| DI water | 0 | 7.28 | 1.17 | 3/3 |
| " | 0 | 7.48 | 1.45 | 3/3 |
| " | 0 | 7.60 | 1.19 | 3/3 |
| glutaraldehyde 2% | 0 | 7.28 | 4.12 | 3/3 |
| AAc (81%) | 0 | 7.60 | 2.87 | 3/3 |
| " | 0 | 7.60 | 2.62 | 3/3 |
| *ozone treated solutions* | | | | |
| DI water | 5 | 7.41 | 2.11 | 3/3 |
| " | 7 | 7.28 | 0.98 | 3/3 |
| " | 31 | 7.60 | 2.30 | 3/3 |
| AAc (81 %) | 144 | 7.60 | >6.60 | 0/3 |
| " | 175 | 7.60 | 4.19 | 1/3 |

DI = deionized
AAc = acetic acid

Fig. 12

Inactivation of Bacillus subtilis spores by ozonated alcohols and glycols

| Precursor solution | Ozonation time | Dilution factor | $Log_{10}$ reduction | Fraction with positive growth |
|---|---|---|---|---|
| Pentanol (C5) | 0 | 1:81 | 1.81 | 3/3 |
| " | 10 | 1:9 | 1.46 | 3/3 |
| " | 10 | 1:81 | 1.45 | 3/3 |
| " | 30 | 1:9 | 1.76 | 3/3 |
| " | 30 | 1:81 | 1.06 | 3/3 |
| " | 90 | 1:81 | 1.51 | 3/3 |
| Octanol (C8) | 0 | 1:9 | 0.95 | 3/3 |
| " | 0 | 1:81 | 1.11 | 3/3 |
| " | 10 | 1:9 | 1.71 | 3/3 |
| " | 10 | 1:81 | 1.42 | 3/3 |
| " | 30 | 1:9 | 1.49 | 3/3 |
| " | 30 | 1:80 | 1.90 | 3/3 |
| " | 90 | 1:9 | 1.81 | 3/3 |
| " | 90 | 1:81 | 1.50 | 3/3 |
| t-butyl alcohol (C4) | 0 | 1:9 | 1.21 | 3/3 |
| " | 0 | 1:27 | 0.96 | 3/3 |
| " | 10 | 1:9 | 1.31 | 3/3 |
| " | 10 | 1:27 | 0.87 | 3/3 |
| " | 30 | 1:9 | 1.43 | 3/3 |
| " | 30 | 1:27 | 1.33 | 3/3 |
| " | 90 | 1:9 | 2.38 | 3/3 |
| " | 90 | 1:27 | 1.25 | 3/3 |
| Ethylene glycol ($CH_2OHCH_2OH$) | 0 | 1:9 | 0.42 | 3/3 |
| " | 0 | 1:27 | 1.39 | 3/3 |
| " | 10 | 1:9 | 0.27 | 3/3 |
| " | 10 | 1:27 | 0.52 | 3/3 |
| " | 90 | 1:9 | 0.94 | 3/3 |
| " | 90 | 1:27 | 0.00 | 3/3 |
| " | 270 | 1:9 | 1.13 | 3/3 |

| | | | | |
|---|---|---|---|---|
| " | 270 | 1:27 | 1.02 | 3/3 |
| | | | | |
| Polyethylene glycol (CH$_2$OHCH$_2$OH)$_n$ | 0 | 1:9 | 1.51 | 3/3 |
| " | 0 | 1:27 | 1.81 | 3/3 |
| " | 10 | 1:9 | 0.73 | 3/3 |
| " | 10 | 1:27 | 0.79 | 3/3 |
| " | 30 | 1:9 | 1.28 | 3/3 |
| " | 30 | 1:27 | 1.13 | 3/3 |
| " | 90 | 1:9 | 1.16 | 3/3 |
| " | 90 | 1:27 | 1.56 | 3/3 |
| " | 270 | 1:9 | 1.13 | 3/3 |
| " | 270 | 1:27 | 1.13 | 3/3 |
| | | | | |
| HD Polyethylene glycol (CH$_2$OHCH$_2$OH)$_n$ | 0 | 1:27 | 1.71 | 3/3 |
| " | 0 | 1:81 | 1.25 | 3/3 |
| " | 10 | 1:27 | 0.00 | 3/3 |
| " | 10 | 1:81 | 0.00 | 3/3 |
| " | 30 | 1:27 | 1.80 | 3/3 |
| " | 30 | 1:81 | 0.00 | 3/3 |
| " | 90 | 1:27 | 2.12 | 3/3 |
| " | 90 | 1:81 | 1.50 | 3/3 |
| | | | | |
| Isopropanol (C3) CH$_3$CHOHCH$_3$ | 0 | 1:3 | 0.57 | 3/3 |
| " | 0 | 1:9 | 0.89 | 3/3 |
| " | 30 | 1:3 | 1.26 | 3/3 |
| " | 30 | 1:9 | 1.72 | 3/3 |
| " | 90 | 1:3 | 5.06 | 3/3 |
| " | 90 | 1:9 | 1.63 | 3/3 |
| " | 270 | 1:9 | 3.86 | 1/3 |
| " | 270 | 1:27 | 1.56 | 3/3 |
| " | 270 | 1:81 | 0.76 | 3/3 |
| | | | | |
| Methanol (C1) | 0 | 1:3 | 1.81 | 3/3 |
| " | 0 | 1:9 | 1.69 | 3/3 |
| " | 30 | 1:3 | 0.00 | 3/3 |
| " | 30 | 1:9 | 1.29 | 3/3 |
| " | 90 | 1:3 | 3.67 | 3/3 |
| " | 90 | 1:9 | 0.88 | 3/3 |
| " | 270 | 1:9 | 1.50 | 3/3 |
| | | | | |

| Ethanol (C2) | 0 | 1:3 | 1.28 | 3/3 |
| --- | --- | --- | --- | --- |
| " | 0 | 1:9 | 1.73 | 3/3 |
| " | 10 | 1:3 | 3.58 | 3/3 |
| " | 10 | 1:9 | 1.96 | 3/3 |
| " | 30 | 1:3 | 4.44 | 1/3 |
| " | 30 | 1:9 | 2.27 | 3/3 |
| " | 90 | 1:3 | >6.66 | 0/3 |
| " | 90 | 1:9 | 4.11 | 2/3 |
| " | 270 | 1:9 | >6.66 | 0/3 |
| " | 270 | 1:27 | >6.66 | 0/3 |
| " | 270 | 1:81 | 4.46 | 3/3 |

METHODS OF PREPARING ANTIMICROBIAL COMPOSITIONS COMPRISING OZONE

This invention was made with Government support under grant 2 R44-AI44739-02 awarded by the National Institutes of Health (NIH). The Government has certain rights in this invention.

BACKGROUND OF THE RELEVANT ART

1. Field of the Invention

The present invention relates to anti-microbial solutions and methods of making and using anti-microbial solutions, especially sporicidal solutions.

2. Background of the Invention

Steam autoclaves can be used to sterilize some medical instruments by subjecting the instruments to superheated steam at high pressures before being depressurized and cooled. One of the drawbacks of the steam autoclave is that many medical instruments cannot withstand the high temperatures and pressures. Another drawback resides in the one to two hour cycle time that is required to achieve sterilization.

Ethylene oxide gas can be used to sterilize some other medical instruments and equipment that cannot withstand the pressure or temperature of the autoclave. The instruments are sealed in a sterilizing chamber and pressurized with the ethylene oxide gas. However, ethylene oxide sterilization requires long cycle times and careful handling of the highly toxic ethylene oxide gas. Furthermore, some medical equipment can not be sterilized with ethylene oxide gas.

Liquid sterilization systems can be used to sterilize equipment that cannot withstand either the autoclave or the ethylene oxide gas. These systems involve immersing the equipment into a vat or tank that has been filled with a sterilizing solution, such as stabilized hydrogen peroxide or glutaraldehyde. Because such liquid sterilizations are normally performed manually, the skill and care of the technician are determining factors in whether sterilization or disinfection is, in fact, attained. In many instances, the components of the anti-microbial composition must be mixed by a technician who may become exposed to the harmful vapors produced by many disinfectants, such as glutaraldehyde. Even when mixed properly, immersion times on the order of six to ten hours are commonly required to assure sterilization. Moreover, many liquid sterilization systems are highly corrosive to metal parts, particularly brass, copper, and aluminum. With long immersion times, even the carbon steel and stainless steel of the medical instruments can become pitted and sharp cutting edges dulled.

Antimicrobial compositions are particularly needed in the food and beverage industries to clean and sanitize processing facilities such as pipelines, tanks, mixers, etc. and continuously operating homogenization or pasteurization apparatus. Other uses for antimicrobial compositions include vegetable washing and disinfection, meat surface decontamination, poultry chiller baths, cleaning of electronic components, treatment of wounds, cleaning in place of food processing equipment, cleaning and disinfecting beverage containers, terminal sterilization, treatment of contaminated infectious waste and elimination of odors.

Sanitizing compositions have been formulated in the past to combat microbial growth in such facilities. For example, Wang, U.S. Pat. No. 4,404,040, teaches a short chain fatty acid sanitizing composition comprising an aliphatic short chain fatty acid, a hydrotrope solubilizer capable of solubilizing the fatty acid in both the concentrate and sanitizing solution, and a hydrotrope compatible acid so that the sanitizing solution has a pH in the range of 2.0 to 5.0.

Ozone has long been recognized as a useful chemical commodity valued particularly for its outstanding oxidative activity. In fact, ozone is the fourth strongest oxidizing chemical known, having an oxidation potential of 2.07 volts. Because of this property, ozone and/or fluid mixtures including ozone are capable of removing a wide variety of contaminants, such as cyanides, phenols, iron, manganese, and detergents, from surfaces. Also, ozonated water is used to "clean", i.e., oxidize, the surface of silicon wafers in-process in the semiconductor industry. Additionally, ozone is also useful for inhibiting, reducing and/or eliminating the accumulation of biomass, mold, mildew, algae, fungi, bacterial growth and scale deposits in various aqueous solution systems. When used in this manner, ozonation provides the advantage of producing a lesser quantity of potentially harmful residues than, e.g., chlorination, which leaves undesirable chlorinated residues in aqueous systems. However, the effectiveness of ozonated water in each of these applications is adversely affected by its low solubility and short-half life (approximately 10 minutes) in aqueous solutions. That is, not only is it difficult to dissolve ozone in an aqueous solution, but also, once dissolved, it is difficult to maintain the ozone in solution.

Ozone has been shown to be inadequate for many medical disinfection and sanitization applications. The disinfection of medical equipment often necessitates use of disinfectants able to deactivate resistant microorganisms, such as bacterial spores. Ozone is a poor sporicidal agent both in the gas phase or dissolved in liquids. This is believed to be due to the slow penetration of ozone through the spore's protective layers. Though this deficiency can be overcome by lengthening the contact time, it is inconvenient and often impractical to do so. Furthermore, ozone does not retain its anti-microbial activity in the presence of interfering compounds, because ozone reacts indiscriminately with dissolved oxidizable substances such that the amount of ozone available for disinfection is drastically reduced.

To counter these limitations, there are several methods of increasing the quantity of dissolved ozone in aqueous solutions, each of these prior art methods has limitations that render them inadequate for certain applications. For example, bubbling ozone directly into water at ambient pressure has been used as a method to dissolve ozone in aqueous solutions. Such a technique, however, does not optimize the quantity of ozone dissolved, since the ozone bubbles effervesce before a substantial amount of ozone can be dissolved into solution and/or before the ozonated water can be applied to the surface to be treated.

European patent application No. EP 0 430 904 A1 discloses a process for producing ozonated water comprising the step of contacting an ozone-containing gas with fine droplets of water. However, this process is less than optimal since it provides limited contact between the ozone-containing gas and water. Additionally, this application does not teach a method of keeping the ozone in solution until it is delivered to a point of use. Thus, it is possible that, upon delivery, a large quantity of the ozone dissolved in solution will effervesce, and the benefits of the mixing process will be lost.

Several methods utilizing cooling to increase the quantity of dissolved ozone in aqueous solutions have also been proposed. For example, U.S. Pat. No. 5,186,841 discloses a method of ozonating water comprising injecting ozone through an aqueous stream across a pressure drop of at least 35 psi. The ozonated stream is then combined with a second stream that is preferably a portion of an aqueous solution that is recirculating in a cooling water system. The resultant stream is forced to flow at a velocity of 7 feet per second for a distance sufficient to allow 70% of the ozone to be absorbed. Additionally, U.S. Pat. No. 4,172,786 discloses a process for increasing the quantity of dissolved ozone in an aqueous solution by injecting an ozone containing gas into a side stream conduit that circulates a portion of cooling water. U.S. Pat. No. 5,464,480 discloses a process for removing organic materials from semiconductor wafers using ozonated water. Specifically, this patent teaches that high ozone concentration water, suitable for use in the disclosed process may be obtained by mixing ozone and water at a temperature of from about 1° C. to 15° C.

The use of pressurized vessels and distribution systems is also a known method of improving the level of dissolved ozone. A system disclosed in U.S. Pat No. 5,971,368 describes a system where by introducing a gas into a pressurized vessel containing a liquid; delivering the resulting admixture to a point of use through a pressurized conduit; and subjecting the admixture to controlled dispensing at the point of use, the quantity of dissolved gas in the liquid is not only enhanced over the quantity of dissolved gas in the liquid at atmospheric pressure, but also, that a substantial portion of the enhanced amount of dissolved gas stays in solution to the point of use.

U.S. Pat. No. 5,662,803 (P. R. Young, Nalco Corporation) discloses use of ozone combined with compounds normally added to water called scale inhibitors, preventing ozone from degrading certain water treatment chemicals. In one example however, (example 5) they examine the effect of ozone combined with an organic additive against bacteria suspended in solution. The bacteria are in a phosphate solution and the additive is propionate (non acid form). The propionate reduces the decay rate of ozone. The example shows that the ozonated propionate solution is more effective against bacteria.

U.S. Pat. No. 5,484,549 describes using ozone introduced into an aqueous solution containing Lewis base compounds. Such bases include sodium hydroxide, potassium hydroxide, sodium orthosilicate, sodium tripolyphosphate, sodium carbonate and sodium bicarbonate. The solutions provide an enhanced surface cleaning effect. A continuation of this patent (U.S. Pat. No. 5,567,444) describes an aqueous cleaning solution that is used as a first treatment, combined with a second liquid containing peroxyacids. The two compositions used consecutively provide improved surface cleaning and surface decontamination.

Numerous inventions relate to the ozonolysis of organic compounds that contain nonaromatic carbon-carbon double bonds. The formation of peroxidic species by ozonolysis of oleic acid is described by Rebovic et al (JAOCS Vol 69, February 1992). This type of ozonolysis reaction is a useful step in the industrial production of carboxylic acids. Typically, the olefinic starting compounds are treated in a solvent with an ozone-containing carrier gas. If the reaction is carried out in aprotic solvents, secondary ozonides are formed. In protic solvents, such as for example alcohols or acids, peroxides are formed, which can occur as polymers. German patent No. 2,713,863 discloses a method of continuously producing an ozonide by ozonizing a high molecular weight olefin oleic acid or linoleic acid in the presence of ester and an organic acid or alcohol. Kigawa et al U.S. Pat. No. 5,292,941 discloses a method for ozonizing an unsaturated fatty acid or a lower alkyl ester thereof providing, amongst other things, efficient removal of the reaction heat. It is usual to further react the ozonolysis products with oxidants to form carboxylic acids. Sometimes peroxyacids are used as the oxidants. Kulpe et al in U.S. Pat. No. 5,591,893 describes such as process emphasizing the role of hydrogen peroxide in the oxidative work up.

Ozonized sunflower oil "Oleozon" has been shown to have antimicrobial effects on bacterial, viruses and fungi (Lezcano et al., Ozone Sci. Engineering 22 (2000) 207–214). Ozone reacts with unsaturated fatty acids present in the oil, and targets carbon-carbon double bonds. Substances produced include hydrogen peroxide aldehydes alpha dihroxy-hydroperoxides and Criegee ozonides. This substance can be applied as a skin treatment agent.

As the term "sanitizing" is used in the method of the present invention, it means a reduction in the population numbers of undesirable microorganisms by about 5 powers (i.e., at least 5 orders of magnitude). The composition may also be used to achieve disinfection or sterilization (i.e., elimination of all microorganisms) by employing higher levels of active biocides in the use solutions. Disinfection and sterilization are truly lethal in their effects. It is to be emphasized that at the lesser strengths the instant use solution provides sanitizing performance. At still lesser strengths, the present invention provides a "biostatic" capability where the organisms, in the presence of the agent are inhibited from growing but upon removal from the agent, it can again multiply.

SUMMARY OF THE INVENTION

The invention includes a method of preparing an antimicrobial solution, comprising the step of ozonating a solution comprising greater than 80 weight percent ethanol and more preferably between 90 and 100 weight percent ethanol. It is suitable to obtain the ethanol from common sources and in common forms, specifically including hydrous (water-containing) ethanol. Optionally, the solution further comprises octanoic acid, preferably between 1 and 40 percent, more preferably between 5 and 25 percent. It is preferable to ozonate the solution until the solution has an oxidation potential of greater than 550 mV. Optionally, the method may include the further step of diluting the ozonated solution with water to a water/ozonated solution ratio of between 1 and 100, preferably between 3 and 81. Preferably, the solution is characterized by sporicidal activity. Finally, the method may optionally include the step of contacting a microbially contaminated surface with the diluted solution. Preferably, the surface is then rinsed to remove the solution.

The invention also includes a method of preparing an antimicrobial solution, comprising the steps of preparing a mixture comprising one or more short chain saturated fatty acids having from 1 to 4 carbon atoms and one or more long chain saturated fatty acids having 5 or more carbon atoms, and ozonating the mixture. The preferred short chain saturated fatty acid is acetic acid and the preferred long chain saturated fatty acid is octanoic acid. In one particularly preferred solution, the mixture comprises between 10 and 20 weight percent octanoic acid and between 80 and 90 weight percent acetic acid. Optionally, the method may further comprise diluting the ozonated mixture with water or other solvent, preferably where the volumetric ratio of the water relative to the ozonated mixture is between 1 and 100. The antimicrobial solution is most preferably sporicidal.

The methods of the present invention may further comprise the steps of measuring the oxidation potential of the mixture, and continuing to ozonate the mixture until the measured oxidation potential is greater than a setpoint, such as about +550 mV. Further, it is optional to electrochemically produce the ozone as needed to ozonate the mixture.

With respect to certain organic compounds, such as octanoic acid, it is preferred that the precursor solution not be diluted before or during ozonolysis, but rather may be substantially diluted following ozonolysis. While these precursor solutions can tolerate minor amounts of water, it is preferred that these solutions be substantially free of water. However, after the mixture or solution has been ozonated, the ozonated mixture may be freely diluted with water while retaining its antimicrobial or sporicidal activity. By contrast, other organic compounds, such as ethanol, are substantially unaffected by the presence of water during ozonolysis.

BRIEF DESCRIPTION OF THE DRAWINGS

So that the above recited features and advantages of the present invention can be understood in detail, a more particular description of the invention, briefly summarized above, may be had by reference to the embodiments thereof which are illustrated in the appended drawings. It is to be noted, however, that the appended drawings illustrate only typical embodiments of this invention and are therefore not to be considered limiting of its scope, for the invention may admit to other equally effective embodiments.

FIG. 1 is a table showing the effect of ozonated octanoic acid in acetic acid on *Bacillus subtilis spores*.

FIG. 2 is a table showing the effect of ozonated octanoic acid on *Bacillus subtilis* spores.

FIG. 3 is a table showing the effect of ozonated valeric acid on *Bacillus subtilis* spores.

FIG. 4 is a table showing the effect of ozonated 95% ethanol solutions on *Bacillus subtilis* spores.

FIG. 5 is a table showing the effect of ozonated 100% ethanol solutions on *Bacillus subtilis* spores.

FIG. 6 is a table showing the inactivation of *Bacillus subtilis* spores using ozonated liquid after 48 hours.

FIG. 7 is a table showing the effect of ozonated octanoic acid in ethanol on *Bacillus subtilis* spores.

FIG. 8 is a table showing the effect of ozonated steric acid in acetic acid on *Bacillus subtilis* spores.

FIG. 9 is a table showing the concentrations of dissolved ozone that can be stored in concentrated acetic acid.

FIG. 10 is a table showing the zone of inhibition for ozonated and unozonated glacial acetic acid.

FIG. 11 is a table showing the effect of ozonated acetic acid on *Bacillus subtilis* spores.

FIG. 12 is a table showing the effect of various ozonated alcohols and glycols on *Bacillus subtilis* spores.

DETAILED DESCRIPTION OF THE INVENTION

The invention relates to a new composition of matter for preventing microbial growth, for surface cleaning and for sanitizing surfaces. The invention is also useful against all types of microorganisms as well as other forms of infectious agents such as prion proteins. The invention involves adding ozone to a mixture of one or more organic compounds. Included in the organic compounds or precursors suitable for this invention include compounds that do not contain carbon-carbon double bonds. The preferred organic compounds or mixtures of compounds include at least one carboxylic acid or at least one alcohol provided in a liquid.

Upon reaction with ozone, one or more new products or active biocides are formed in the liquid. The ozone is substantially quenched during ozonolysis. The new products have a substantial capability to disinfect, to remove soil from surfaces and to sanitize surfaces. Notably, the new compounds can inactivate bacterial spores within protein films and therefore have high-level disinfection capabilities in the presence of other oxidizable substances. The liquid containing the active biocide can be substantially diluted to low concentrations in aqueous streams yet maintain their effectiveness. The invention also teaches the use of compositions that limit the decomposition of the active biocides.

The antimicrobial compositions or solutions of the present invention are unexpectedly effective in both killing and preventing growth of unwanted microorganisms, including spores. The invention provides an antimicrobial agent useful in water. This water can be used for cleaning medical instruments or for transport or processing of food products. The water may be used as a general purpose disinfection solution for use in applications including but not limited to: medical instruments and products, treatment of medical wastes, dental products, contact lenses in laundry process, cooling towers, animal carcass rinsing, sewage treatment, elimination of pathogens from live animals and plants. The consumption of the present compositions may also be low because they can be diluted into an aqueous stream where the compositions retain much of their effectiveness. Furthermore, only small amounts of the compositions may be needed, even in the presence of organic loading on surfaces to be cleaned.

In addition, the antimicrobial solutions find particular application in conjunction with automated sterilizing or disinfecting of medical instruments and will be described with particular reference thereto. However, it is to be appreciated that the present invention will find utility in sterilizing and disinfecting a wide range of objects, either automatically or manually.

In one embodiment, the active biocide is formed by ozonating a carboxylic acid. Generally, carboxylic acids have the formula R—COOH, where the R may represent any number of different groups including aliphatic groups, alicyclic groups, aromatic groups, heterocycic groups, all of which may be saturated or unsaturated as well as substituted or unsubstituted. Carboxylic acids have a tendency to acidify aqueous compositions in which they are present, since the hydrogen atom of the carboxy group is active and the carboxy group may appear as an anion.

Carboxylic acids found to be useful in the present invention include: acetic acid, propionic acid, butyric acid, glutaric acid, lactic acid, citric acid, formic acid, isobutyric acid, valeric acid, isovaleric acid, pivalic acid, lauric acid, myristic acid, palmitic acid, and stearic acid. Another class of useful compounds are saturated aliphatic dicarboxylic acids including, but not limited to: ethanedioic acid, oxalic acid, malonic acid, succinic acid, glutaric acid, adipic acid, pimelic acid, suberic acid, azelaic acid, sebacic acid, acrylic acid, propiolic acid, methacrylic acid, crotonic acid, isocrotonic acid, oleic acid, elaidic acid, maleic acid, fumaric acid, citraconic acid, and mesaconic acid. Yet another type of useful compounds are unsaturated monocarboxylic acids including, but not limited to, sorbic acid. A further type of useful compounds are carbocyclic carboxylic acids including, but not limited to, camphoric, benzenecarboxylic, benzoic, phtalic, isophthalic, terephthalic, napthoic, toluic, hydratropic, atropic, and cinamic. A still further class of useful compounds are heterocyclic carboxylic acids including, but not limited to, furoic, thenoic, nicotine, isonicotinic. Unsaturated aliphatic monocarboxylic acids useful in the present invention include: oleic acid, linoleic acid, linolenic acid, eleostearic acid, parinaric acid, elaidic acid, ricinoleic acid, caproleic acid, myristoleic acid, palmitoleic acid, petroselinic acid, erucic acid, brassidic acid, arachidonic acid, and mixture thereof.

The preferred carboxylic acids or mixtures of carboxylic acids used in the present invention include long chain (C6–C18) fatty acids. Specific examples of preferred long chain carboxylic fatty acids include such saturated fatty acids as hexanoic (C6), enanthic (heptanoic) (C7), caprylic (octanoic) (C8), pelargonic (nonanoic) (C9), capric (decanoic) (C1 0), undecyclic (undecanoic) (C11), lauric (dodecanoic) (C12), trideclic (tridecanoic) (C13), myristic (tetradecanoic) (C14), palmitic (hexadecanoic) (C16), and stearic (octodecanoic) (C18). These acids can be derived from both natural and synthetic sources. Natural sources include animal oils, vegetable fats or oils that should be fully hydrogenated, and tall oils. Synthetic acids can be produced by the oxidation of petroleum wax. Particularly preferred perfatty acids, also referred to as peroxyacids, for use in the composition of the invention are linear monocarboxyl aliphatic fatty acids, such as octanoic acid, decanoic acid, or mixtures thereof. Preferred short chain (C1–C4) carboxylic acids for use in the composition of the invention include acetic acid, propionic acid, glycolic acid, succinic acid, or mixtures thereof. For the present invention, it is often most preferable to mix a long chain (C6–C18) fatty acid precursor (e.g. octanoic acid) with a short chain (C1–C4) carboxylic acid (e.g. acetic acid) during the ozonation process.

Certain non-carboxylic acids are also useful in accordance with the present invention as organic compounds capable of being ozonated to form active biocides. These substances can include alcohols, such as methanol, ethanol, propanol, pentanol and octanol. Aldehydes are also useful including formaldehyde and acetaldehyde. Non aqueous solvents such as dimethyl carbonate, methyl formate, and dimetyl sulfoxide, are useful. Other oxidants such as hydrogen peroxide are also useful.

Preferred Compositions

In certain embodiments, it is preferable to perform the formation of active biocides in a liquid that contains at least one low molecular weight or short chain organic acid, aldehyde, alcohol or related solvent type molecules. When ozonized, these low molecular weight compounds can produce stabilized ozonolysis products. In certain embodiments it is preferable to perform ozonolysis on liquids containing a relatively high molecular weight or long chain fatty acid molecule (C6–C18) in the presence of a low molecular weight organic acid, aldehyde or alcohol. The presence of the low molecular weight component prevents or limits the rate of decomposition of the ozonolysis products, some of which may be formed from the long chain fatty acid molecule. The low molecular weight compounds are generally unreactive with ozone or have reduced reaction towards ozone compared to larger molecular weight precursors. The term "precursor", as used herein, refers to the compound prior to reaction or exposure to ozone.

The low molecular weight component may include, but is not limited to, one or more of the following: acetic acid, dehydroacetic acid, monohalogenacetic acid, propionic acid, lactic acid, benzoic acid ascorbic acid, citric acid, sorbic acid, formic acid, malic acid, tartaric acid, adipic acid, succinic acid glutaric acid, salicyclic acid, methanol, ethanol, phenyletyl alcohol, isopropyl alcohol, benzyl alcohol, propanol, dimetyl carbonate, methyl formate, dimethyl sulfoxide and mixtures thereof. It is known that many of the low molecular weight components mentioned above by themselves (i.e., without ozone) have known antimicrobial properties and can contribute to the overall antimicrobial effect, increasing the potency of the resulting ozonized compositions. Mixtures containing certain of these compounds may require the presence of water. Furthermore, the presence of at least one low molecular weight compound aids the solubility of starting compounds or precursors and particularly aids the solubility the biocidal reaction products.

Furthermore, it is sometimes desirable to dilute certain precursors (e.g. octanoic acid, oleic acid, steric acid) to lesser concentrations before performing ozonolysis. For octanoic acid and similar organic compounds, it is preferable to use the low molecular weight substances described above as diluents in combination with, or instead of, water and in some instances it may be critical to obtaining sporicidal activity that little or no water is present in solution during ozonolysis. By contrast, ethanol and similar organic compounds may be diluted with various diluents, including water which causes very little reduction in the antimicrobial activity of the ozonated solution.

In a preferred embodiment of the invention, active biocides are formed by ozonating a saturated carboxylic acid, preferably octanoic acid, where acetic acid may act as the solvent or diluent to comprise 10–95% by weight of the liquid to be ozonated. In the preferred mode, octanoic acid may comprise 1–35% by weight of the liquid to be ozonated. It is also preferred, when preparing a biocide with sporicidal strength, that the octanoic/acetic acid liquid to be ozonated is substantially free from water. However, acetic acid has the formula $CH_3COOH$, which is generally freely soluble in water, thereby facilitating dilution of the active biocide following ozonolysis. Alternatively, biocides with much weaker activity may be formed with water present during ozonolysis.

Ozone for ozonating the organic compounds is preferably generated on-site just prior to being dissolved into the reaction medium containing the precursor(s). Within practical limits, shortening the distance between points of generation and use reduce the decomposition loss of the concentration of ozone in the material. The half life of ozone in neutral solutions is on the order to 3–10 minutes and less as pH increases.

Weak concentrations of ozone may be generated using ultraviolet radiation. Typical production of ozone is made using electrical corona discharge. The process requires a source of oxygen, such as pure $O_2$, atmospheric oxygen (air), or enriched air. The source of $O_2$ is passed between electrodes across which a high voltage alternating potential is maintained. The electrodes are powered from a step transformer using service current. The potential is established across the electrodes that are configured to prevent arcing. As oxygen molecules enter the area of the potential, a corona is created having a proportion of free atomic oxygen ions from dissociated $O_2$. The high-energy atomic ions (O) when combined with oxygen ($O_2$) form a mixture of oxygen and ozone. These generators are available commercially. The ozone-containing gaseous mixture is generally directly contacted with an aqueous solution through bubbling or other gas dispersion techniques to introduce a concentration of ozone into the aqueous medium. The contact between water and the aqueous medium is engineered to maximize the absorption of ozone when compared to the rate of decomposition of ozone in the alkaline aqueous medium and the required ozone concentration of the water.

Alternatively, ozone can be made from the decomposition of water in an electrolysis process where ozone is formed at the anode (positive electrode). An electrode for ozone formation can be formed from a variety of materials including lead dioxide, manganese oxide, carbon, platinum, and diamond materials, but most preferably lead dioxide. The cathode can be of a type suitable to form hydrogen from protons. Alternatively, the cathode is a type suitable to form water by the combination of protons and oxygen. Ozone is formed when an electrical current is applied between the electrodes. The ionic conductivity between the electrodes can be accomplished using a liquid electrolyte. In some cases the liquid electrolyte can be substituted by an ion exchange membrane, which serves as the electrolyte. Electrolytic ozone generators generally produce ozone gas at concentrations between about 12 and about 15 wt %. Certain electrolysis processes can generate ozone at concentrations significantly greater than 15 wt %.

The activity of ozone in the compositions of the invention can be improved by introducing ozone bubbles having the smallest possible diameter into the solution. Small bubbles promote the mass transfer of ozone into aqueous solution. Additionally, surface active agents which lower the gas-liquid interfacial tension can be used to enhance ozone gas transport to the liquid medium. Rapid dissolution of ozone can reduce the tendency to off-gas, and cause reactions with solution components to produce oxidized species and promote the effective use of ozone. Alternatively, ozone can be produced using ultraviolet light or combinations of these methods. Neutral aqueous solutions have a low, but measurable, solubility of ozone at various temperatures, as set out in the following table:

| Temperature | Ozone Concentration |
| --- | --- |
| 0. degree. C. | 35 (ppm) |
| 20. degree. C. | 21 |
| 40. degree. C. | 4 |
| 60. degree. C. | 0 |

The stability of ozone in aqueous solution decreases as the temperature decreases indicating the need for temperature control. "Measured ozone" in a given liquid is the apparent concentration of ozone (as $O_3$) in aqueous solution. These aqueous levels of 0.1–40 mg/L (ppm) can be achieved, depending upon a number a factors, including the type of ozone generator used. Electrolytic ozone generators have the potential to form dissolved ozone concentrations higher than can be achieved by corona discharge or UV generators. The difference between the ozone and measured ozone relates to an amount of ozone "equivalents" that apparently become stored in aqueous solution by reaction with precursor species to form ozonized or oxidized inorganic materials, e.g., hydroxyl radicals, ozonide radical ion, superoxide radical ion, peroxygen compounds etc. Such oxidized materials tend to be a source of oxidizing potential.

We have found that the sanitizing power of the materials of the invention relate to the presence of free solubilized ozone "equivalent" species and the presence of species that can act as oxidizing agents created in-situ by the reaction of ozone with materials in solution. The term "active" ozone composition refers to the total concentration of oxidizing species (organic and inorganic) produced by introducing ozone into the formulated cleaners of the invention. The term "initial ozone" means the measured concentration of ozone immediately after introduction of ozone into the aqueous solution. The difference between initial ozone and measured ozone relates to timing of the measurement. "Measured ozone" is the concentration of ozone in solution measured at any time after an initial value is found.

In aqueous cleaning compositions using ozone, the concentration of the ozone, and oxidizing ozone byproducts, should be maintained as high as possible to obtain the most active cleaning and antimicrobial properties. Due to the decomposition of ozone and the limited solubility of ozone in the liquids of the present invention, the level of ozone may be below what can be detected. However, there remains a high amount of oxidizing species, ("ozone equivalents").

Various optional materials may be added to the compositions of the invention to help solubilize the fatty acids, solubilize ozonolysis products, restrict or enhance the formation of foam, to control hard water, to stabilize the composition, or to further enhance the antimicrobial activity of the composition.

The compositions of the invention can contain a surfactant hydrotrope coupling agent or solubilizer that permits blending short chain fatty acids and species derived therefrom in aqueous liquids. Functionally speaking, the suitable couplers that can be employed are non-toxic and retain the fatty acid and the perfatty acid in aqueous solution throughout the temperature range and concentration to which a concentrate or any use solution is exposed. The hydrotrope coupling agent can comprise about 0.1 to 30 wt %, preferably about 1 to 20 wt %.

Any hydrotrope coupler may be used provided it does not react with the other components of the composition or negatively affect the antimicrobial properties of the composition. Representative classes of hydrotropic coupling agents or solubilizers which can be employed include anionic surfactants such as alkyl sulfates and alkane sulfonates, linear alkyl benzene or naphthalene sulfonates, secondary alkane sulfonates, alkyl ether sulfates or sulfonates, alkyl phosphates or phosphonates, dialkyl sulfosuccinic acid esters, sugar esters (e.g., sorbitan esters) and C8–C10 alkyl glucosides. Preferred coupling agents for use in the present invention include n-octanesulfonate, available as NAS 8D from Ecolab, and the commonly available aromatic sulfonates, such as the alkyl benzene sulfonates (e.g. xylene sulfonates) or naphthalene sulfonates.

Some of the above hydrotropic coupling agents independently exhibit antimicrobial activity at low pH. This adds to the efficacy of the present invention, but is not the primary criterion used in selecting an appropriate coupling agent. Since it is the presence of perfatty acid in the protonated neutral state which provides biocidal activity, the coupling agent should be selected not for its independent antimicrobial activity but for its ability to provide effective interaction between the substantially insoluble perfatty acids described herein and the microorganisms which the present compositions control.

Compounds such as mono-, di- and tri-alkyl phosphate esters may be added to the composition to suppress foam. Such phosphate esters would generally be produced from aliphatic linear alcohols, there being from 8 to 12 carbon atoms in the aliphatic portions of the alkyl phosphate esters. Alkyl phosphate esters possess some antimicrobial activity in their own right under the conditions of the present invention. This antimicrobial activity also tends to add to the overall antimicrobial activity of the present compositions even though the phosphate esters may be added for other reasons. Furthermore, the addition of nonionic surfactants would tend to reduce foam formation and enhance performance of the other components of the composition, particularly in cold or soft water. A particularly useful nonionic surfactant for use as a defoamer is nonylphenol having an average of 12 moles of ethylene oxide condensed thereon and being encapped with a hydrophobic portion comprising an average of 30 moles of propylene oxide.

Chelating agents can be added to the compositions of the invention to enhance biological activity, cleaning performance and stability of the active biocides. For example, 1-hydroxyethylidene-1,1-diphosphonic acid commercially available from the Monsanto Company under the designation "DEQUEST" can be used. Chelating agents can be added to the present composition to control or sequester hardness ions such as calcium and magnesium. In this manner, both detergency and sanitization capability can be enhanced.

Other materials that are sufficiently stable at the low pH contemplated by the present compositions may be added to the composition to impart desirable qualities depending upon the intended ultimate use. For example, phosphoric acid ($H_3PO_4$) can be added to the compositions of the invention. Additional compounds can be added to the concentrate (and thus ultimately to the use solution) to change its color or odor, to adjust its viscosity, to enhance its thermal (i.e., freeze-thaw) stability or to provide other qualities that tend to make it more marketable.

The composition of the invention can be formulated from solutions containing carboxylic acids or alcohols. In some instances alcohols may be combine with carboxylic acids. Subsequently, ozonation is performed for sufficient time to produce active biocides. The aforementioned additives can be formulated into the disinfection solution prior to ozonation, during ozonation or after ozonation.

Additives may also include other antimicrobial agents. Often two or more antimicrobial agents are combined, because the killing effects of two antimicrobial agents used together often exceeds the sum of the killing effects of the two agents applied separately. Antimicrobial additives may include chlorine-containing species including, but not limited to: free chlorine, liquid bleach (hypochlorite HClO) chlorine dioxide, and organochlorine compounds such as chloramine, dichloramine and dichlorocyanuric acid compounds. Additives may include iodine-containing compounds such as diatomic iodine ($I_2$), hypoiodous acid (HI) or iodophors where iodine is solubilized by means of an appropriate surface active agent. Additional additives may include peroxygen-type disinfectants, such as hydrogen peroxide ($H_2O_2$) and peracetic acid ($CH_3COOOH$). Surface active agents with antimicrobial properties may include amphoteric surfactants containing cationic groups (e.g. Tego Disinfectants) and surface active agents formed from acid anionic compounds e.g. dodecyl benzene sufonic acid, oleic acid, sodium salt sufonated, and dodecyl benzene sufonic acid. There are many types of quaternary ammonium compounds that can be added including benzalkonium chlorides, two chain quaternareies, cetylpyidinium chloride, N-(3 chloroallyl)hexaminium chloride, domiphen bromide, benzethonium chloride, methylbenzethonium chloride. Many phenolic compounds can be added, such as bisphenols, Bis(hydroxyphenyl)alkanes, nitrophenols, aminophenols, hydroxyquinoline and dervivates thereof. Phenolic compounds include chloro and polybromo derivatives of phenol and of betanapthol. Possible additives include alcohols such as ethanol and methanol, phenylethyl alcohol, and isopropyl alcohols. Formaldehyde and glutaraldehyde are optional ingredients. A variety of nitrogen containing compounds including thiazoles, quinolines, mercaptobenzothiazoles, pyridines are options to be included. Another potential additive is chlorohexidine, a cationic bisbiguanide.

PREPARATION OF ACTIVE BIOCIDES

Preparation of active biocides on-demand from precursors may be accomplished in an automated fashion, as well as manually. Preparation of active biocides requires: (1) a contact chamber containing the liquid to be ozonated and (2) a source of ozone. These elements are connected via a conduit through which a gas, enriched with ozone, is passed. The contact chamber contains a means of introducing ozone into the liquid to be ozonated. The invention uses a means for controlling the rate at which ozone gas is being introduced to the liquid. Control of the rate of ozone flow into the liquid, and the duration of treatment, can control the quantity of active biocide generated per unit time. The contact chamber contains a means of being periodically replenished with liquid from which the active biocides are formed.

A variety of embodiments known to those skilled in the art, are possible for the mixing chamber, particularly with reference to how ozone is introduced into the liquid. For instance a venturi device, located in a side stream in fluid communication with the contacting chamber can be used in certain embodiments. Fluid flow can be diverted from the contacting chamber through the venturi device where in ozone is introduced. The ozonated liquid is subsequently returned to the contact chamber. Liquid circulation through the venturi enables ozone to be continuously added to the liquid containing the active biocide precursors. The contact chamber also contains a means of dispensing ozonated solutions, such as an outlet port in fluid communication with a device for using the ozonated solutions to clean microbially contaminated surfaces.

Ozone gas concentrations prior to contacting the liquid can be measured as can the concentration of ozone in the gas exiting the contact chamber. The oxidizing potential of this solution, can be measured by a standard, commercially available, ORP (oxidation-reduction potential) probe. An ORP greater than +550 mV may indicate the conditions are met necessary for proper sanitation efficiency. Gas phase measurements of ozone concentrations are typically made by UV absorbance devices. The amount of ozone dissolved in the liquid at any one time may be measured, such as through the oxidation-reduction potential measurement (see above). Both the amount of ozone enriched gas and the time of contact may be controlled by this method. It may be appropriate to use other oxidation indicators. A variety of indicators can be used to measure residual ozone, including, paper strips, chemical indicators or electrochemical probes.

The temperature of the liquid during ozonation can change during the process of forming the active biocides. Generally, the temperature is observed to increase during ozonolysis. Monitoring of the temperature is carried out to indicate the degree to which the formation of active biocides is taking place. Temperature measurements can be used in conjunction with process control, fault diagnosis, quality control and quality assurance. Small changes in temperature, or a slow rate of change in temperature can indicate insufficient progress towards forming active biocides. Alternatively, failure to reach sufficient temperatures or slow rate of change in temperature can indicate depletion of one or more of the necessary ingredients in the liquid being ozonated, or that insufficient ozone is being applied to solution. Adjustments to the process of the invention can be made accordingly. By monitoring that sufficient temperatures are attained, it is possible to validate that a sufficient concentration of active biocides has been formed. Temperature increases of 10° C. or more are indicative of the formation of active biocides from their precursors. Temperature changes may be measured by probes, such as thermocouple probes, both within and in the vicinity of the contact chamber or any point in the process where ozone and liquids come into contact.

Cooling may be applied to control the temperature of the liquids used in the invention. Many methods for cooling liquids may be applied. Cooling for instance can be applied using a water jacket surrounding the contact chamber that is used in combination with a source of chilled water. The purpose of the cooling is primarily to ensure that optimum temperatures for active biocides are not exceeded and that heat damage to equipment and fittings does not occur. Temperatures of greater than 75° C. can be considered excessive, at which point cooling may be initiated.

In certain embodiments it may be desirable to maintain the starting liquids in an unreacted form until disinfection is required. This can be achieved using one or more storage vessel for the precursors, additives and diluents. Volumes of the required ingredients are metered into a reaction chamber, mixed, then ozonated, optionally without any operator intervention. The batch of ozonated liquid forms a use solution that is applied to microbially contaminated surface and discarded. Optionally, a batch may make only the amount of active biocide necessary for a single unit operation. The operation of the process requires refilling of a reservoir vessel when depleted of starting chemicals. It should also be recognized that the antimicrobial solutions of the present invention may be made by continuous or semi-batch processes as well.

The ozonated liquid containing the active biocide can be further processed into "use solutions". It may be efficacious to use the ozonated liquid as a concentrate from which many different compositions containing active biocides may be formulated. After ozonation, all or part of the resulting liquid containing active biocides may be mixed with other types of liquids or the optional additives described above. The formulation of use solutions may be performed in the contact chamber or the ozonated fluid may be transferred to a separate vessel for subsequent reformulation. In one embodiment, it may be preferable to add the ozonated liquids to an aqueous stream. Alternatively, the ozonated liquid may be mixed with a stream consisting predominantly of non-aqueous solvents. For many uses, it is preferable to use the ozonated liquids in a substantially diluted form.

Processes of the invention can be carried out automatically, where events such as addition of ozone to the liquid, dilution of the ozonated liquid, refilling treatment reservoirs and contacting tanks, activating conduits, pumping fluids, introduction of additives and formulation of use solutions may be performed using integrated timers, valves, electronic controls, relays and computer programs. The automated steps of the invention can be aided by the use of sensors, actuators and gages to monitor parameters such as: fluid levels, gas and liquid pressures, temperature, liquid flow and gas flow.

Often is it desirable to recover the disinfection solution containing active biocides after use, such that the liquid containing active biocides can be reused. The used disinfection solution after contact with an object (e.g. medical instrument) can be directed to a container where it can be retained until needed again. Multiple reuse is possible. If needed, additional ozone gas can be applied to the liquid in this container or the liquid transferred to a contact chamber for additional ozonation. Active biocides in the use solutions can therefore be replenished from time to time.

Heating of the use solution may be performed to enhance its efficacy, such that contact times required to achieve the required levels of sanitation are reduced. Suitable temperatures for disinfection and sanitation with active biocides range from 4–95° C.

A skilled person can see that there are may variations on the methods by which the biocide precursors and ozone can be brought together and there are many methods by which formulation of use solutions can be performed. The process of the invention, as described above, is essentially a batch process. However, it is possible to form active biocides in a continuous process using an in-line mixing and ozonation method. Such a process may involve flowing an aqueous stream through a chamber, where the chamber is configured with inflow and outflow ports, such that continuous flow may occur through the chamber. Ozone may be introduced into the chamber by a suitable contacting means and, at the same time, precursors from which active biocides are formed are introduced into the chamber. All agents necessary for the formation of active biocides can be introduced on a continuous basis. The flow rate through the chamber and the liquid volume are proportioned to allow sufficient fluid retention time for adequate active biocide formation. Similarly ozone contacting is configured such that there is sufficient contact time between the ozone and the liquid precursors for active biocides to form. In this embodiment, active biocides are formed continuously and are present in the exit stream from the contact chamber.

Equipment necessary to carry out the formation of active biocides may be integrated with existing equipment, for example the process of the invention may be incorporated into devices including, but not limited to, endoscope reprocessors, catheter washers, hemodialysis machines and laundry machines. It is possible to incorporate the items of the invention, namely the source of ozone, ozone contacting chamber and appropriate methods for dispensing and recovery of the use solutions into said processing equipment, such that the process of the invention and the means of using the active biocides can be implemented as a single unit process.

The process of the invention incorporates a means to generate and dispense rinse water of high microbioloical quality. Rinse water is generally applied as a final treatment step to remove solutions employed in the sanitation or cleaning processes. A suitable rinse solution can be made by directing ozone-enriched gas to a separate contactor chamber, where the contactor contains an aqueous solution. Ozone is contacted with the water for a sufficient time to eliminate substantially all microorganisms from the water. The treated water is dispensed and directed to the item that has first been previously contacted with a cleaning or sanitizing solution of this invention or otherwise. The disinfected rinse water removes excess disinfectant or cleaning agents. The advantage of this invention is that both the sanitizer and sterile rinse water are derived as a single unit process. Moreover the use of a rinse solution treated with ozone is preferable because ozone is a potent means of eliminating microorganisms from water and it decomposes rapidly without leaving a chemical residue.

Ozone may also be applied directly to the surface or item to be cleaned or sanitized. Such a treatment would consist of a tank or bath to hold the precursor liquid of the present invention. The tank includes provisions for introducing an ozone rich gas into the liquid. The object to be sanitized or cleaned can be immersed directly in the tank such that ozonation of the liquid and cleaning and sanitization occur simultaneously. While the precursor liquid may be undiluted during ozonolysis, it is preferred for many on site applications that the precursor liquid be used in a diluted concentration although the there will be a lower ozone efficiency for converting the precursor to the active biocide?] The cleaned item may be further rinsed with water before being removed from the tank. This method may be particularly suitable for treating certain food items, electrical components or engine parts.

Ozone is substantially quenched when it is introduced into a liquid containing any of the aforementioned precursors to active biocides. Problems of handling ozone off gases are therefore reduced. Use of certain liquids of the present invention do not substantially quench ozone therefore ozone vapors may accumulate or be released. The present invention embodies techniques known to those skilled in the art for containing or eliminating ozone vapors. Remediation methods can include, adsorption beds of activated carbon or metal catalysts such as manganese dioxide that promote ozone decomposition.

USES OF ACTIVE BIOCIDES

The present compositions are useful in the cleaning or disinfecting of equipment in the health care industries. Examples of items that can be disinfected include endoscope reprocessors, catheters, hemodialysis machines etc. Additionally, the compositions can be used for the sanitizing of processing facilities or equipment in the food service or food processing industries. Examples of process facilities in which the composition of the invention can be employed include a milk line dairy, a continuous brewing system, food processing lines, such as pumpable food systems, and beverage lines. Food service wares can also be disinfected with the composition of the invention. The composition is also useful in sanitizing or disinfecting solid surfaces such as floors, counters, furniture, medical tools and equipment found in the health care industry. Such surfaces often become contaminated with liquid body spills such as blood, other hazardous body fluids or mixtures thereof.

It is generally recommended that the actual cleaning of the in-place system or other surface (i.e., removal of unwanted organic material) is accomplished with a different material such as a formulated detergent (or this composition modified for detergent effect) that is introduced with cold or heated water. After this initial cleaning step, the present compositions would be applied or introduced into the system at a suitable solution concentration in unheated, ambient temperature water. The present composition is found to remain in solution in cold (e.g., 40° F./4° C.) water and heated (e.g., 140° F./60° C.) water. Although it is not normally necessary to heat the aqueous solution of the present composition, under some circumstances heating may be desirable to further enhance its antimicrobial activity.

A method of sanitizing substantially fixed in-place process facilities, such as an endoscope reprocessor comprises the following steps. The composition of the invention is introduced into a rinsing bowl or chamber that houses the item to be sterilized. The temperature of the use solution is in the temperature range of about 4 to 60° C. After introduction of the solution, the solution is circulated throughout the system (i.e., through the channels of the endoscope) and on the external surface of the endoscope for a time sufficient to sanitize the process facilities (i.e., to kill undesirable microorganisms). After the system has been sanitized by means of the present composition, the solution is drained from the system. The composition can be recovered in a vessel for reuse. Upon completion of the sanitizing step, the system optionally may be rinsed with other materials such as potable water, in some circumstances the water can be ozonated to render it free of microorganisms then used as rinse water. The composition is preferably circulated through the process facilities for 5–10 minutes or less. Upon completion of sterilization such rinsing is usually mandatory with circulation for longer periods of time.

The composition may also be employed by dipping medical or food processing equipment into the solution, soaking the equipment for a time sufficient to sanitize the equipment, and wiping or draining excess solution off the equipment. The composition may be further employed by spraying or wiping food processing surfaces with the solution, keeping the surfaces wet for a time sufficient to sanitize the surfaces, and removing excess solution by wiping, draining vertically, vacuuming, etc.

The composition of the invention may also be used in a method of sanitizing hard surfaces such as institutional type equipment, utensils, dishes, health care equipment or tools, and other hard surfaces. The composition may also be employed in sanitizing clothing items or fabric that have become contaminated. The composition is contacted with any of the above contaminated surfaces or items at temperatures in the range of about 4° C. to 60° C., for a period of time effective to sanitize, disinfect, or sterilize the surface or item. For example, the composition can be injected into the wash or rinse water of a laundry machine and contacted with contaminated fabric for a time sufficient to sanitize the fabric. Alternatively, the composition can be formed in situ in the laundry device by mixing the precursors with ozone. Excess amounts of the solution can then be removed by rinsing or centrifuging the fabric.

The following examples are intended to illustrate the above invention and should not be construed as to narrow its scope. One skilled in the art will readily recognize that these examples suggest many other ways in which the present invention could be practiced.

WORKING EXAMPLES-ACTIVE BIOCIDES

Preparation of Carriers. In each of the following examples, the disinfection solutions were evaluated using spores of *Bacillus subtilis*. Spores were placed onto glass carriers formed by cutting microscope slides in half lengthways. Slides were placed in a culture tube that was capped and sterilized prior to inoculation with spores. A total of 0.1 mL of a spore suspension containing 10% bovine serum albumin by weight was placed onto a small area near one end of the slide. Approximately 20 $\mu$L (microliters) of spore suspension was added at a time for 5 times, allowing each 20 $\mu$L amount to dry between additions. Heat drying was performed by briefly holding the slide over a flame. The heat-fixed culture was stored in the refrigerator until needed for up to, but no longer than, 5 days.

Disinfection of Carriers. In the following examples, three vials were prepared, each containing 200 mL of the disinfectant composition to be evaluated. One spore carrier was placed into each vial. The spore carriers were held in the disinfection solutions for 30 minutes. After contacting was complete, the carriers were removed from the disinfection solutions using forceps and rinsed with sterile saline.

Spore Recovery and Enumeration. After rinsing, each of the slides was placed in a sterile tube containing 2 mL of saline. The tube was sonication in an ultrasonic bath for at least an hour. The slides were then removed. The remaining saline solution was diluted serially then plated out onto nutrient agar media in duplicate using the spread plate technique. Invert plates were incubated at 37° C. and counted after 24 hours. Duplicate plate counts were averaged and the surviving spores reported units of CFU/carrier (colony forming units per carrier). Calculation of the disinfection efficiency involves conversion of the pre-and post-disinfection counts to the $\log_{10}$ system and subtracting the post-disinfection from the pre-disinfection count.

Pre-disinfection Counts. To establish pre-disinfection counts, 3 representative spore carriers were selected from each batch prepared and subjected to the spore recovery and enumeration procedure described above, without exposure of the carrier to disinfection solutions.

Preparation of Disinfection Solutions. In each of the examples below, approximately 200 mL of the liquid to be ozonated was placed in a glass flask. Ozone was introduced into the solution through a diffuser such that fine bubbles of ozone-bearing gas were introduced into the liquid. The source of the ozone gas was a Lynntech Model 124 PEM electrochemical ozone generator operating at 1–1.5 Amps per square centimeter. The gas flow rate was 1 liter per minute. The ozone concentration in the gas prior to contacting the liquid was typically 13% by weight. Gas phase ozone measurements were made using a UV spectrophotometer operating at a wavelength of 254 nm. Cooling was accomplished by placing the ozonation glass vessel into a beaker of chilled water.

EXAMPLE 1

In this example, a disinfection solution was prepared by adding pure octanoic acid (OAc) into pure acetic acid (AAc), such that the final concentration of octanoic acid was 15% by volume. The liquid was ozonated as described above. Samples of the ozonated liquid were withdrawn after 10, 30 and 90 minutes. Each of the withdrawn samples were added to sterile distilled water to give dilutions of 1:3, 1:9, 1:27 and 1:81. The temperature of the ozonated liquid was between 40 and 50° C. when the dilution was carried out. The sporicidal properties of the samples were evaluated as described above using a contact time of 30 minutes. For comparison purposes, a liquid containing 100% AAc (no OAc) was ozonated for 90 minutes, diluted in water and evaluated for sporicidal capabilities. In addition, the following non-ozonated liquids were evaluated: octanoic acid (16%) in acetic acid, acetic acid (9%) in water, acetic acid (81%) in water, and glutaraldehyde (2%).

Each data point in the example is the result of triplicate carrier tests that have been averaged. The results shown in FIG. 1 illustrate that the ozonated OAc/AAc liquids have exceptional sporicidal capabilities. The highest levels of kills were achieved with the samples ozonated for 90 minutes. High levels of kill were achieved even with samples that were substantially diluted in water. In general, longer ozonation times improved the potency of the resulting liquid. However, even the OAc/AAc samples that were ozonated for 10 minutes and diluted 1:3 with water were able to eliminate all spores. Ozonated AAc only was considerably less effective as a disinfectant than the ozonated OAc/AAc mixture. Non-ozonated acetic acid at considerable strength (81% by weight in water) also did not compare favorably to the ozonated OAc/AAc mixtures. Finally, the ozonated OAc/AAc mixtures, even when diluted, gave superior disinfection results to a 2% commercial glutaraldehyde solution (Nu Cidex, available from Johnson & Johnson). This is surprising, since glutaraldehde is one of the most effective disinfection agents used in hospitals to decontaminate equipment.

EXAMPLE 2

100% OAc was ozonated for 10, 30 and 90 minutes. Cooling was applied during the ozonation process. The cooled solution was diluted then contacted with the glass spore carriers for 30 minutes. The results shown in FIG. 2 show that ozonated OAc gives rise to active biocides with an exceptional ability to eliminate spores. The result also shows that longer ozonation times increases the killing efficiency of the resulting liquids.

EXAMPLE 3

15% valeric acid (VAc) in AAc was ozonated for 10, 30 and 90 minutes. Cooling was applied during the ozonation process. The cooled solution was diluted then contacted with the glass spore carriers for 30 minutes. The results shown in FIG. 3 show that ozonated VAc gives rise to active biocides with the ability to eliminate spores. Valeric acid was ozonated for the same time and under the same conditions as the OAc/AAc liquids in example 1. All things being equal, the liquid resulting from the ozonation of VAc was reduced in its ability to kill spores compared to a similar OAc/AAC mixture. However, longer ozonation times increase the killing efficiency of a mixture containing VAc.

EXAMPLE 4

The sporicidal activity of various ozonated ethanol solutions was investigated. Cooling was applied during the ozonation of the liquids listed in the FIG. 4. The ethanol solutions varied in their water content. If ozonated for sufficient time, liquids containing ethanol showed surprising high levels of spore deactivation, comparing favorably with a commercial glutaraldehyde solution.

EXAMPLE 5

In accordance with the procedures set out above, ozonated 100% ethanol was tested and shown to be a potent antimicrobial agent. The results set out in FIG. 5 that sufficient ozonation leads to a very strong antimicrobial, biocidal, and even sporicidal agent.

EXAMPLE 6

The sporicidal activity of two ozonated liquids: (i) OAc (15%) in AAc and (ii) pure OAc, was investigated and compared. Ozonation was performed for 90 minutes followed by a 48 hour storage period at 25° C. Then the liquids were diluted in sterile distilled water and evaluated for sporicidal activity as described above. The results shown in FIG. 6 indicate that OAc(15%) in AAc had a substantially higher efficiency against spores than the ozonated Oac (100%). For instance, no viable spores were recovered from any of the carriers placed in the 1:81 dilution of the OAc/AAc liquid. In contrast, relatively high numbers of viable spores were recovered from the carriers placed in the ozonated OAC. When both liquids are freshly ozonated then tested for sporicidal activity almost immediately (see e.g. Examples 1 and 2) both ozonated liquids were efficient at eliminating spores. The comparative results over a period of storage demonstrates that improvments in the amtimicrobial properties of ozonated carboxylic acids can be achieved by inclusion of a low molecular weight compound, such as acetic acid in the liquid to be ozonized.

EXAMPLE 7

Active biocides were formed by the ozonation of a solution containing a saturated fatty acid, octanoic acid, in a solution consisting predominantly of an alcohol, ethanol. The tests compare non-ozonated ethanol, ozonated ethanol, and ozonated ethanol containing 15% OAc. The ozonation of ethanol enhances its ability to disinfect compared to non-ozonated ethanol. FIG. 7 shows that the disinfection capability of ozonated ethanol is further enhanced by the inclusion of OAc in ethanol at the time the ozonation is performed.

EXAMPLE 8

Active biocides were formed by the ozonation of a solution containing a saturated fatty acid, steric acid, in a solution consisting predominantly of acetic acid. The active biocides were prepared as described above. FIG. 8 shows the results of the testing.

WORKING EXAMPLES - DISSOLVED OZONE CONCENTRATIONS

In examples 1–8, ozone was introduced into a liquid where it reacted with organic compounds to form new products with antimicrobial properties. The ozone introduced into the liquid was essentially quenched or consumed in the process of being added to the liquid. The examples 9–10 that follow illustrate that certain liquids enable surprisingly high dissolved ozone concentrations to be achieved and that the resulting solutions have superior antimicrobial properties. Example 11 illustrates the antimicrobial activity of the solutions formed in accordance with examples 9–10.

EXAMPLE 9

>400 ppm Dissolved Ozone

Solutions containing varying amounts of acetic acid were saturated with ozone. Solutions were prepared containing 50%, 75%, 90%, 95%, and 99% by volume acetic acid in water. In separate experiments, 100 mL of the above solutions were placed in 250 mL round bottom flasks fitted with a ground glass top. The top contained two fittings that permitted gas flow in through one fitting and gas flow out through the other. A mixture of ozone and oxygen was delivered from Lynntech's Model 124 Electrochemical Ozone generator to the solution through a stainless steel gas diffusing stone. The flow rate was approximately 1,000 mL of gas per minute, and the concentration of ozone was 10% by weight. The solutions were ozonated for 5 minutes and the concentration of dissolved ozone was determined by the indigo colorimetric method. An additional solution of 100 mL of deionized water and a solution of 100 mL of glacial acetic acid were also ozonated.

The concentration of dissolved ozone was determined by the indigo colorimetric method. An indigo stock solution was prepared by adding 500 mL of deionized water and 1 mL of phosphoric acid to a 1 L volumetric flask. 770 mg of potassium indigo trisulfonate was added to the flask, and stirring was continued until the dye was completely dissolved. The flask was filled to the mark with deionized water. A working indigo solution was prepared by adding 20 mL of indigo stock solution, 10 g of sodium dihydrogen phosphate ($NaH_2PO_4$), and 7 mL of concentrated phosphoric acid to a 1 L volumetric flask. The flask was filled to the mark with deionized water. The concentration of ozone in solution was determined by adding an aliquot of ozonated solution (typically 30 $\mu$L) to 3 mL of working indigo solution in a 1 cm path-length quartz cuvette. The cuvette was capped with a piece of parafilm and inverted a few times to mix the solutions. As a blank, the same volume the equivalent non-ozonated solution was added to 3 mL of working indigo solution in a matched cuvette and mixed. The blank was placed in the reference position of a Shimadzu model 2101 PC double beam UV/Vis spectrophotometer. The cuvette that contained the ozonated sample was placed in the sample position. The absorbance at 600 nm was measured to provide the difference in absorbance between the blank and the sample. The concentration of ozone in solution is simply:

mg $O_3$/L=$(V_w \times \Delta A)(f \times b \times V_s)$ where $\Delta A$ is the difference in absorbance between the sample and the blank, b is the path-length of the cuvette, $V_w$ is the volume of working indigo solution, $V_s$ is the volume of sample, and f is 0.42. f is based on a sensitivity factor of 20,000/cm for the change in absorbance at 600 nm per mole of ozone added per liter. It was calibrated by iodometric titration. The ratio of $V_w$ to $V_s$ was typically 100 for concentrations at or below 80 ppm. For solutions above 80 ppm, the ratio of $V_w$ to $V_s$ was 1000 (30 $\mu$L sample plus 30 mL working indigo solution).

FIG. 9 is a graph of dissolved ozone concentration as a function of the mole fraction of acetic acid in water. The graph shows that unexpectedly high concentrations of ozone were obtained in the acetic acid solutions. Only about 30 ppm ozone was possible in DI water, compared to ozone concentrations greater than 400 ppm in pure acetic acid. The results also show that, as the ratio of acetic acid to water increases, high dissolved ozone concentrations are favored. These high levels were achieved without using a pressurized vessel and without anything other than conventional methods for bubbling ozone into solution.

EXAMPLE 10

Wet Disc Inhibition Studies

This example illustrates improved biocidal activity of ozonated acetic acid, where high concentrations of dissolved ozone are achieved. Glacial acetic acid was ozonated for minutes, and the resulting solution was tested for antimicrobial effectiveness using the zone of inhibition test. This test consisted of spreading 100 $\mu$l of *Psuedomonas aeruginosa* on nutrient agar plates, then dipping a 13 mm nitrocellulose disk in the solution to be tested. The disk was then placed gently onto the nutrient agar plates containing *P. aeruginosa*. After 24–48 hours, a lawn of bacteria would grow, with a zone containing no cells around the disk. The presence and size of this zone indicated the effectiveness of the antimicrobial agent being tested. The size of the zone is reported as the diameter of the zone in mm.

Solutions that were tested included (i) glacial ozonated acetic acid immediately after ozonation, (ii) glacial ozonated acetic acid 16 hours after ozonation, as well as (iii) a control of unozonated glacial acetic acid. These solutions were diluted down to 50%, 25%, 12.5%, 6.2%, 3.2%, and 1.6% acetic acid by volume with water, then tested using the zone of inhibition test.

The results shown in FIG. 10 demonstrates the effectiveness of ozonated acetic acid as an antimicrobial agent. Concentrations as low as 1.6% show significant antimicrobial properties. The ozonated glacial acetic acid that was tested after 16 hours is slightly less effective than ozonated acetic acid tested immediately after ozonation. However, both ozonated acetic acids (fresh and stored) performed better that unozonated acetic acid. Freshly ozonated water containing ozone concentrations at 25ppm or greater (no acetic acid) gave no zone of inhibition when applied to the wet disc.

EXAMPLE 11

200 mL of 81% acetic acid by volume (in DI water) water was ozonated in a glass flask. 10 wt % ozone gas was generated electrochemically by the method described above. The ozone gas flow rate through the solutions was 1000 mL per minute. After ozonation of the liquid was performed for 10 minutes, the liquid was transferred to a beaker. Three spore carriers were placed in the beaker. At the same time a liquid sample was withdrawn from the beaker and its ozone concentration measured by the method described above. The spore carriers were kept in the ozonated acetic acid solution for exactly 30 minutes. They were then removed, washed and the number of viable spores remaining was enumerated as described above. The data set out in FIG. 11 are averages obtained from three spore carriers. Non-ozonated controls were performed with deionized water, acetic acid (81% in water) and a commercial glutaraldeyde solution.

FIG. 11 shows that ozonated acetic acid achieved a high level of spore deactivation. No viable spores were recovered from some of the carriers. The initial ozone concentration at the time the spore carriers were immersed was high, 125 ppm and 175 ppm ozone, accounting for the high levels of spore deactivation. The ozonated acetic acid compared favorably to a commercial glutaraldehyde solution. However, the dissolved ozone concentration decreased over the 30 minute contact time. By comparison, the non-ozonated 81% acetic acid was relatively ineffective as a sporicidal agent. These solutions were able to achieve a 2.87 log reduction at best. DI water that had been ozonated gave initial ozone concentrations not exceeding 31 ppm and was, not surprisingly, unable to achieve high levels of spore inactivation. The best that was achieved was a 2.3 log reduction in viable spores.

EXAMPLE 12

Various alcohols were ozonated and tested for activity against *Bacillus subtilis* spores. The alcohols tested included pentanol, octanol, t-butyl alcohol, ethylene glycol, polyethylene glycol, high density polyethylene glycol, isopropanol, methanol and ethanol. Each of the alcohols were tested with no ozonation and with ozonation for different time periods, variously including 10, 30, 90 and/or 270 minutes, using the 10 wt % ozone at 1000 mL/min described in earlier examples. The resulting ozonated alcohols were then variously diluted by factors of 3, 9, 27 or 81 as shown in FIG. 12. The Figure illustrates that a surprisingly greater $\log_{10}$ reduction of spores was achieved using ethanol than with any of the other alcohols investigated under similar ozone exposure and water dilution conditions.

The term "comprising" means that the recited elements or steps may be only part of the device and does not exclude additional unrecited elements or steps.

While the foregoing is directed to the preferred embodiment of the present invention, other and further embodiments of the invention may be devised without departing from the basic scope thereof, and the scope thereof is determined by the claims which follow.

What is claimed is:

1. A method of preparing an antimicrobial solution, comprising:

(a) ozonating a solution comprising greater than 80 weight percent ethanol.

2. The method of claim 1, wherein the solution further comprises octanoic acid.

3. The method of claim 1, wherein the solution comprises between 90 and 100 weight percent ethanol.

4. The method of claim 1, wherein the ozonated solution has an oxidation potential of greater than 550 mV.

5. The composition formed by the method of claim 1.

6. The method of claim 1, further comprising:

(b) diluting the ozonated solution with water to a water/ozonated solution ratio of between 1 and 100.

7. The method of claim 1, further comprising:

(b) diluting the ozonated solution with water to a water/ozonated solution ratio of between 3 and 81.

8. The method of claim 3, the solution being characterized by sporicidal activity.

9. The method of claim 1, wherein the step of ozonating further comprises introducing a volume of ozone gas that is a multiple of between 5 and 135 times the volume of the solution.

10. A method for cleaning a surface, comprising:

(a) ozonating a precursor solution comprising ethanol to form an active biocide solution;

(b) diluting the active biocide solution wherein said solution is greater than 0.3% by weight of ethanol with water to a water/active biocide solution ratio of between 1 and 100 to form a use solution; and (c) contacting a microbially contaminated surface with the use solution.

11. The method of claim 10, further comprising:

(d) rinsing the surface to remove the use solution.

12. The method of claim 10, further comprising:

(d) ozonating water to form sterile rinse water; and (e) contacting the surface with the sterile rinse water to remove the use solution.

13. The method of claim 10, further comprising:

(d) reusing the use solution on another microbially contaminated surface.

14. The method of claim 13, further comprising:

(e) ozonating the use solution before reusing the use solution.

15. A method of preparing an antimicrobial solution, comprising:

(a) preparing a mixture comprising one or more short chain saturated fatty acids having from 1 to 4 carbon atoms wherein the total concentration of fatty acids is greater than 5% by weight and one or more long chain saturated fatty acids having 5 or more carbon atoms; and (b) ozonating the mixture.

16. The method of claim 15, wherein the one or more short chain saturated fatty acids comprise acetic acid.

17. The method of claim 15, wherein the one or more long chain saturated fatty acids comprise octanoic acid.

18. The method of claim 15, wherein the one or more short chain saturated fatty acids comprises acetic acid and the one or more long chain saturated fatty acids comprises octanoic acid.

19. The method of claim 18, wherein the mixture comprises between 10 and 20 weight percent octanoic acid and between 80 and 90 weight percent acetic acid.

20. The method of claim 15, further comprising:

(c) diluting the ozonated mixture with water.

21. The method of claim 20, wherein the volumetric ratio of the water relative to the ozonated mixture is between 1 and 100.

22. The method of claim 15, wherein the antimicrobial solution is sporicidal.

23. The method of claim 15, further comprising:

(c) measuring the oxidation potential of the mixture; and (d) continuing to ozonated the mixture until the measured oxidation potential is greater than a setpoint.

24. The method of claim 23, wherein the setpoint is about +550 mV.

25. The method of claim 23, further comprising:

(e) electrochemically producing the ozone as needed to ozonate the mixture.

26. The method of claim 15, wherein the mixture is substantially free of water.

27. The method of claim 26, wherein the ozonated mixture is diluted with water.

28. A method of preparing an antimicrobial solution, comprising:
   (a) preparing a mixture consisting essentially of one or more short chain saturated fatty acids having from 1 to 4 carbon atoms wherein the total concentration of fatty acids is greater than 5% by weight and one or more long chain saturated fatty acids having 5 or more carbon atoms; and
   (b) ozonating the mixture.

29. The method of claim 28, wherein the one or more short chain saturated fatty acids comprises acetic acid and the one or more long chain saturated fatty acids comprises octanoic acid.

30. The method of claim 29, wherein the octanoic acid concentration is between 10 and 20 weight percent and the acetic acid concentration is between 80 and 90 weight percent.

31. The method of claim 28, further comprising:
   (c) diluting the ozonated mixture with water to a volumetric ratio of water to ozonated mixture between 1 and 100.

32. The method of claim 28, wherein the mixture is substantially free of water.

33. A method of preparing an antimicrobial solution, comprising:
   (a) ozonating a solution comprising aqueous ethanol in an amount greater than 0.3% by weight.

34. The method of claim 33, wherein the aqueous ethanol is greater than 6 weight percent ethanol.

35. The method of claim 33, wherein the aqueous ethanol is greater than 18 weight percent ethanol.

36. The method of claim 33, further comprising:
   allowing the ozone to react with the ethanol to form an active biocide.

37. The method of claim 33, wherein the ozone is substantially quenched during ozonolysis.

38. The product formed by the method of claim 1.

39. The method of claim 33, wherein the pH is less than 7.

40. The method of claim 1, wherein the pH is less than 7.

41. The method of claim 10, wherein the pH is less than 7.

42. The method of claim 15, wherein the pH is less than 7.

43. The method of claim 28, wherein the pH is less than 7.

44. The method of claim 10, further comprising:
   allowing the ozone to react with the ethanol to form the active biocide.

45. The method of claim 10, wherein the ozone is substantially quenched during ozonolysis.

* * * * *

UNITED STATES PATENT AND TRADEMARK OFFICE
CERTIFICATE OF CORRECTION

PATENT NO.    : 6,468,953 B1
DATED         : October 22, 2002
INVENTOR(S)   : Hitchens et al.

It is certified that error appears in the above-identified patent and that said Letters Patent is hereby corrected as shown below:

<u>Title page,</u>
Item [75], Inventors, correct the spelling of the last name of the first listed inventor from "Hitchems" to -- Hitchens --.

Signed and Sealed this

Eleventh Day of February, 2003

JAMES E. ROGAN
*Director of the United States Patent and Trademark Office*